United States Patent
Postolov et al.

(10) Patent No.: US 8,208,713 B2
(45) Date of Patent: Jun. 26, 2012

(54) METHOD AND SYSTEM FOR INSPECTING A DICED WAFER

(75) Inventors: Yuri Postolov, Afula (IL); Menachem Regensburger, Shimshit (IL)

(73) Assignee: Camtek Ltd., Migdal Haemek (IL)

( * ) Notice: Subject to any disclaimer, the term of this patent is extended or adjusted under 35 U.S.C. 154(b) by 446 days.

(21) Appl. No.: 12/350,243

(22) Filed: Jan. 8, 2009

(65) Prior Publication Data

US 2009/0116726 A1    May 7, 2009

Related U.S. Application Data (63) Continuation-in-part of application No. 12/064,355, filed as application No. PCT/IL2006/000996 on Aug. 29, 2006, now abandoned.

(60) Provisional application No. 61/020,409, filed on Jan. 11, 2008.

(51) Int. Cl.
*G06K 9/00* (2006.01)

(52) U.S. Cl. .......................................... 382/145; 702/95

(58) Field of Classification Search .................. None
See application file for complete search history.

(56) References Cited

U.S. PATENT DOCUMENTS

| | | | | |
|---|---|---|---|---|
| 5,495,535 | A | * | 2/1996 | Smilansky et al. ........... 382/145 |
| 6,826,298 | B1 | * | 11/2004 | O'Dell et al. ................. 382/149 |
| 2004/0057611 | A1 | * | 3/2004 | Lee et al. ...................... 382/145 |

\* cited by examiner

*Primary Examiner* — Jason M Repko
*Assistant Examiner* — Siamak Harandi
(74) *Attorney, Agent, or Firm* — Reches Patents (57) ABSTRACT

A method for inspecting a diced object that comprises multiple dies, the method includes: acquiring multiple images of multiple portions of the diced object, starting from a first portion that comprises an alignment area and continuing through adjacent portions of the diced object; assigning a die index to each die of the multiple dies of the diced object, starting from a die of the first portion and continuing through adjacent portions of the diced object; associating between dies of the diced object and a dies of a reference object in response to the assigned indexes and locations of the dies of the diced object; wherein the reference object is not diced; and comparing between a die of the diced object and another die while taking into account an association between the die of the diced object and a reference object die.

19 Claims, 13 Drawing Sheets

METHOD AND SYSTEM FOR INSPECTING A DICED WAFER

RELATED APPLICATIONS

This application claims priority of U.S. provisional patent Ser. No. 61/020,409, titled "A method and system for inspecting a diced wafer" filed on 11 Jan. 2008.

This application is a continuation-in-part (CIP) of U.S. patent application Ser. No. 12/064,355, titled "An inspection system and a method for inspecting a diced wafer", filed on 6 Sep. 2011, now abandoned, which is a national stage entry of International Application No. PCT/IL06/00996 filed on 29 Aug. 2006.

FIELD OF THE INVENTION

This application relates to methods for inspecting diced wafers and an inspection system.

BACKGROUND OF THE INVENTION

Figure 1:
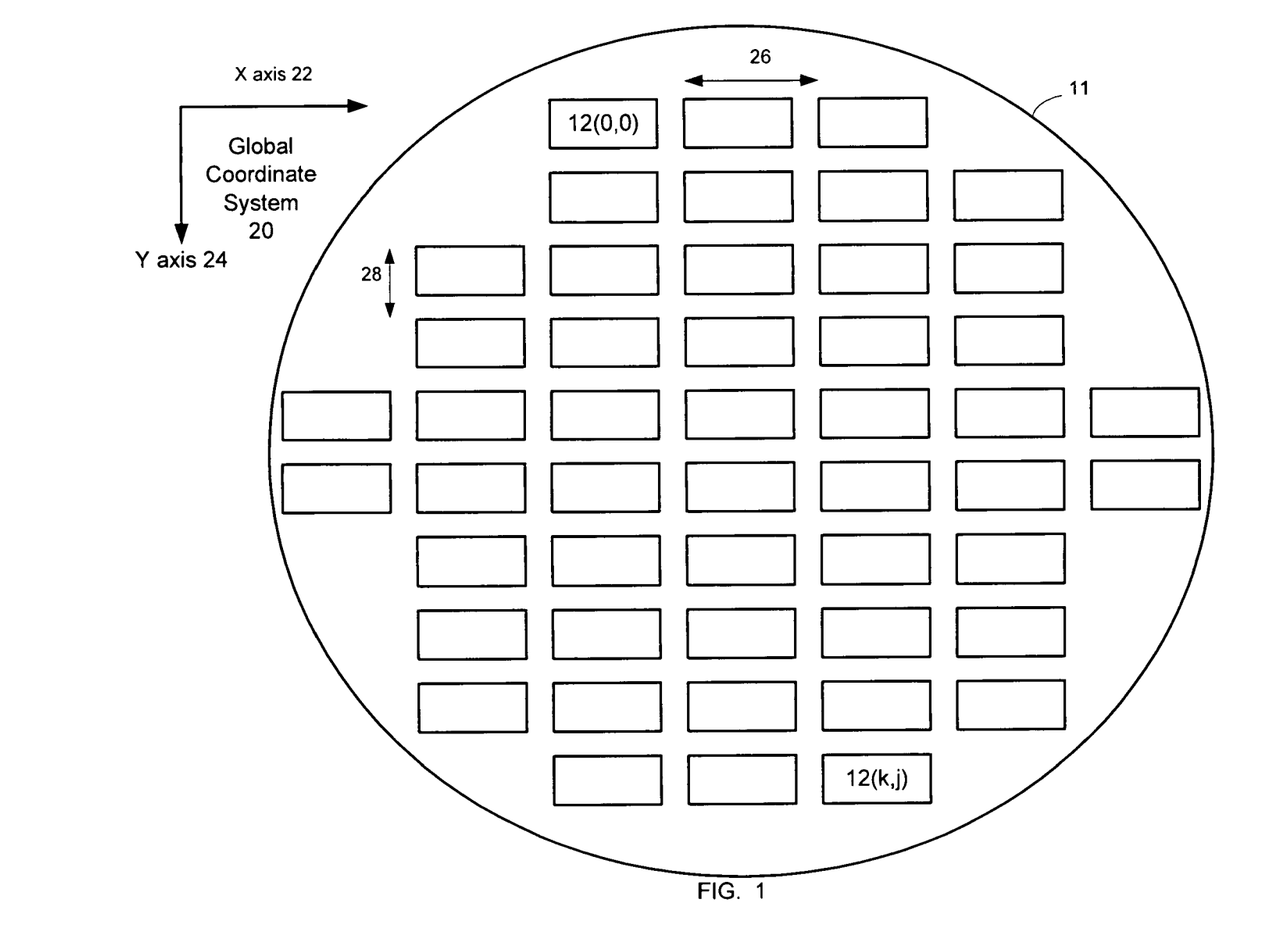
FIG. 1 illustrates a prior art wafer.

Integrated circuits are manufactured by a highly complex and costly manufacturing process. During the first stages of this process a wafer is formed. A wafer includes multiple dice that are arranged in an ordered array of dice wherein the dice are parallel to each other, as illustrated in FIG. 1. Rectangular-shaped dice are arranged in columns and rows and are separated by scribe lines. The dice are characterized by a die X axis pitch 26 and a die Y axis pitch Y 28. Referring to FIG. 1, wafer 11 includes multiple dice 12(0,0)-12(k,j) that are collectively denoted 12. FIG. 1 also illustrates a global coordinate system 20 that includes X-axis 22, and Y-axis 24. The dice are arranged in parallel to these imaginary axes and are aligned with global coordinate system 20.

Figure 2:
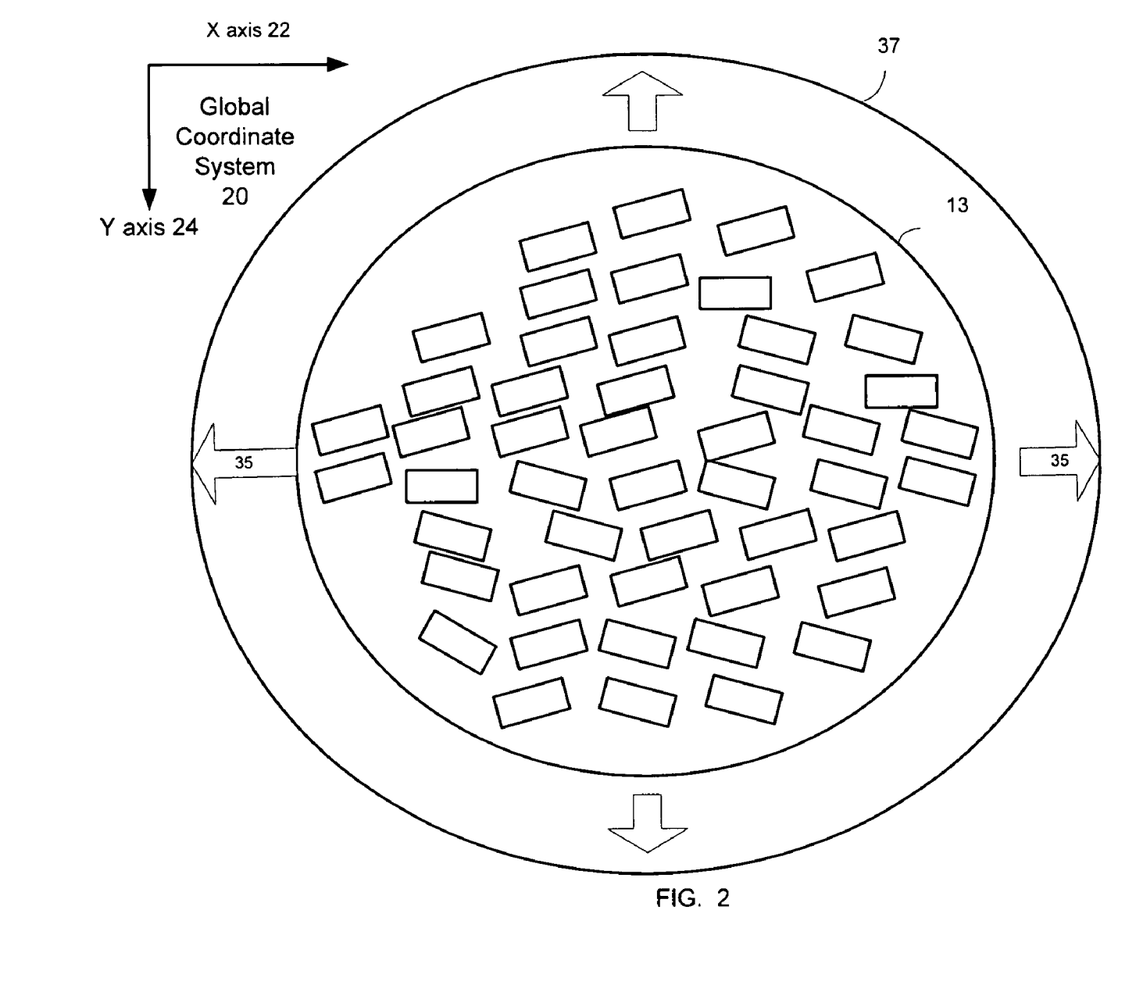
FIG. 2 illustrates a prior art diced wafer and the forces that expand the diced wafer.

During the final manufacturing stages of the wafer the wafer is diced (or sawn) in order to separate between the different dice. The wafer is usually placed on a tape and after the dicing process the dice are then pulled away from each other, conveniently by using an ideally radial force. FIG. 2 illustrates a diced wafer 13, tape 37 and the forces (illustrated by arrows 35) that expand the diced wafer.

The sawing as well as the dice separation process results in a non-linear spatial relationships between the dice of the diced wafer. Each die can be shifted, rotated, sheered and stretched in relation to its previous (pre-dice) position and in relation to adjacent dice.

Figure 3:
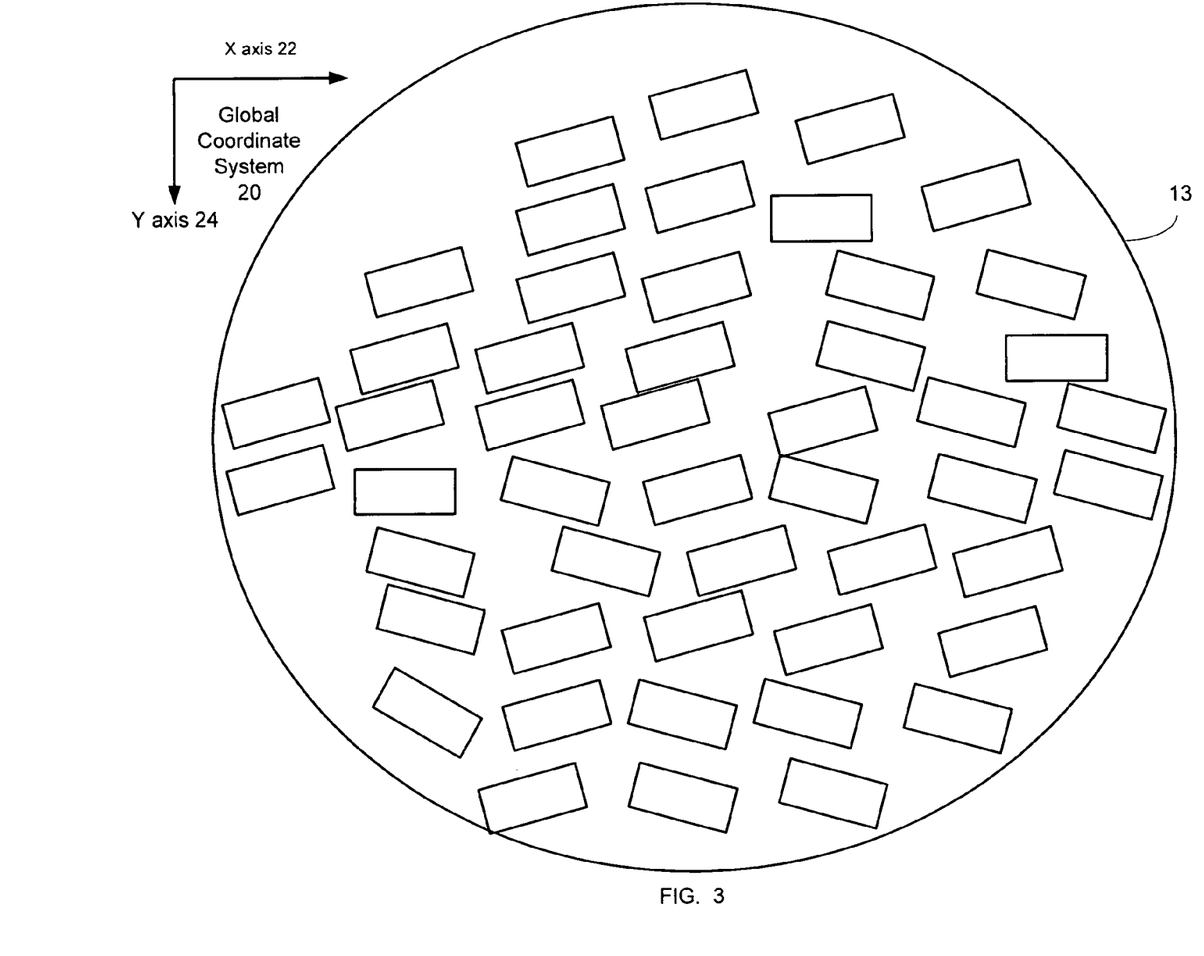
FIG. 3 illustrates a prior art diced wafer.

FIG. 3 illustrates an exemplary diced wafer 13. The dice (collectively denoted 14) of diced wafer 13 are not parallel to each other and diced wafer 13 is also misaligned (rotated) in relation to global coordinate system 20. The latter rotation can result from angular misalignments as well as mechanical inaccuracies.

Wafers and diced wafers are inspected for defects. The inspection can involve comparing between a die and a reference die. The following patents, all being incorporated herein by reference, illustrate various wafer inspection devices and methods as well as registration and alignment methods: U.S. Pat. No. 5,610,102 of Gardopee et al., U.S. Pat. No. 6,021,380 of Fredriksen et al., U.S. Pat. No. 6,937,753 of O'Dell et al., U.S. Pat. No. 6,324,298 of O'Dell et al., and U.S. Pat. No. 4,981,529 of Tsujita.

Various prior art diced wafer inspection methods included locating a unique feature, comparing its location to an expected location, changing the scanning pattern in response to the differences between the actual location to the expected location and continuing to the next expected location of the unique feature.

There is a need to provide an inspection system that can inspect diced wafers and a method for inspecting diced wafers.

SUMMARY OF THE INVENTION

A system for inspecting a diced object that comprises multiple dies, the system includes: an image acquisition unit configured to acquire multiple images of multiple portions of the diced object, starting from a first portion that comprises an alignment area and continuing through adjacent portions of the diced object; a processor, configured to: assign a die index to each die of the multiple dies of the diced object, starting from a die of the first portion and continuing through adjacent portions of the diced object; associate between dies of the diced object and a dies of a reference object in response to the assigned indexes and locations of the dies of the diced object; wherein the reference object is not diced; and compare between a die of the diced object and another die while taking into account an association between the die of the diced object and a reference object die.

A method for inspecting a diced object that comprises multiple dies, the method includes: acquiring multiple images of multiple portions of the diced object, starting from a first portion that comprises an alignment area and continuing through adjacent portions of the diced object; assigning a die index to each die of the multiple dies of the diced object, starting from a die of the first portion and continuing through adjacent portions of the diced object; associating between dies of the diced object and a dies of a reference object in response to the assigned indexes and locations of the dies of the diced object; wherein the reference object is not diced; and comparing between a die of the diced object and another die while taking into account an association between the die of the diced object and a reference object die.

BRIEF DESCRIPTION OF THE DRAWINGS

The present invention will be understood and appreciated more fully from the following detailed description taken in conjunction with the drawings in which.

DETAILED DESCRIPTION OF THE DRAWINGS

Various embodiments of the invention are herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Conveniently, a diced wafer map is generated and a die index is associated with each die of the diced wafer. Multiple images are acquired conveniently according to a predefined image acquisition scheme that defines diced wafer scanning patterns. The method does not require stopping the scanning process in order to adjust the scanning pattern in response to differences between an actual location of a unique feature and the expected location of this feature.

According to an embodiment of the invention the predefined image acquisition scheme includes defining a certain scanning pattern that is not altered in response to detections of unique features or the associations of dice with dice indexes. Scanning patterns can include rater scan patterns but this is not necessarily so.

Figure 4:
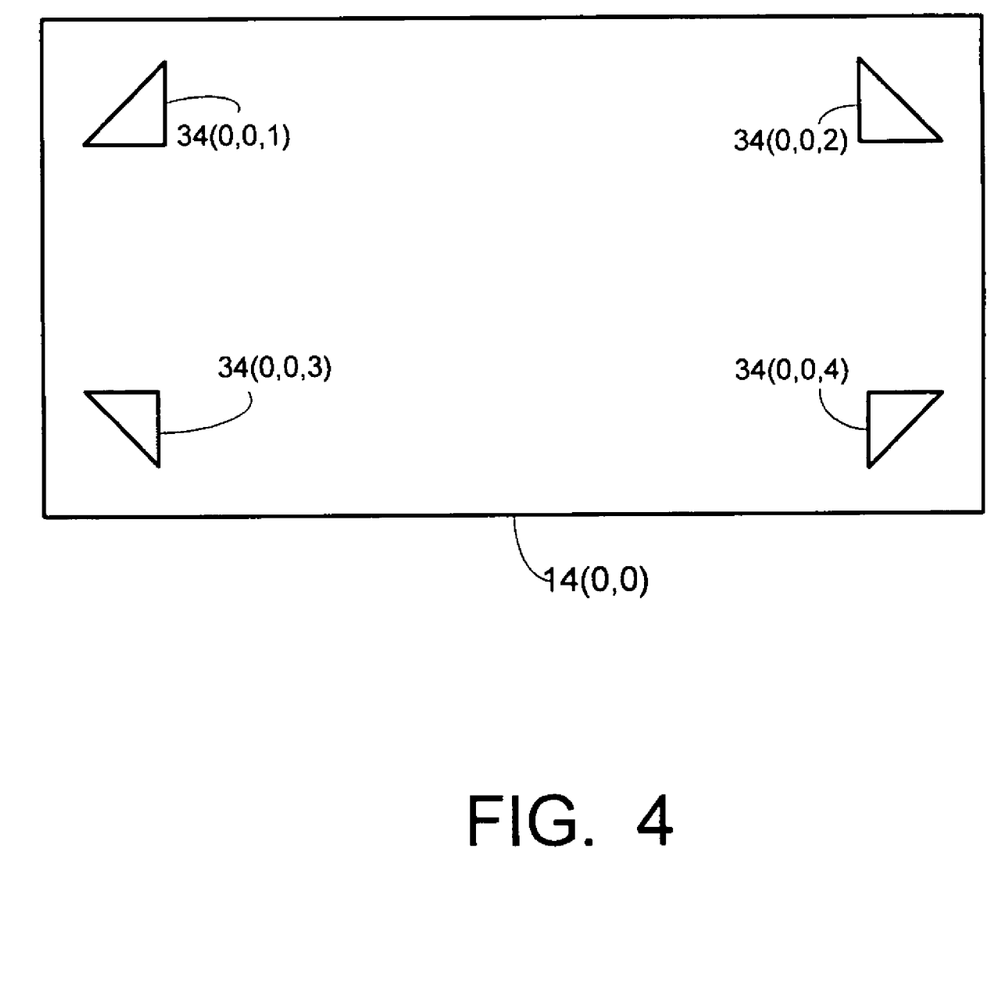
FIG. 4 illustrates a die that includes multiple unique features.

FIG. 4 illustrates a die 14(0,0) that includes four unique features 34(0,0,1)-34(0,0,4). These unique small features are not removed due to the dicing process. Once two or more unique features are identified the orientation of die 14(0,0) as well as its position can be determined.

Figure 5:
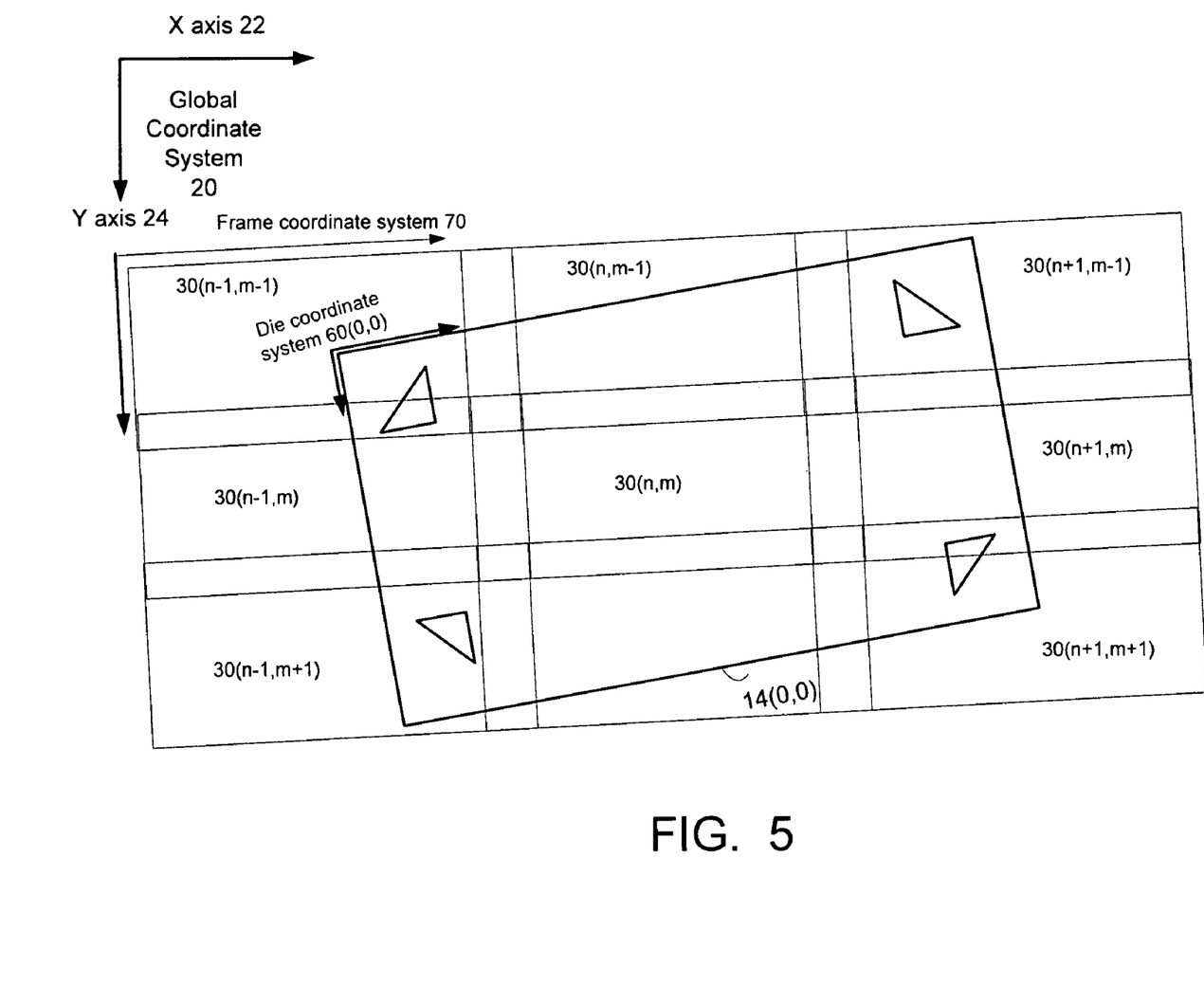
FIG. 5 illustrates multiple images, a die and three coordinate systems according to an embodiment of the invention.

FIG. 5 illustrates multiple images 30(n−1,m) 30(n+1, m+2), die 14(0,0) and three coordinate systems according to an embodiment of the invention.

Die 14(0,0) defines a die coordinate system 60(0,0). Each die of diced wafer 13 defines its own coordinate system. These die coordinate systems are usually not aligned with global coordinate system 20.

FIG. 5 also illustrates multiple images (also referred to as frames) that represent the images that are acquired by an image acquisition unit. These images are aligned with a frame coordinate system 70. Conveniently, the different die coordinate systems are not aligned with the frame coordinate system 70. Frame coordinate system 70 can be aligned with global coordinate system 20 but this is not necessarily so, as illustrated by FIG. 5. This misalignment can result from mechanical inaccuracies of the inspection system as well as from other reasons. Typically, the spatial relationship between global coordinate system 20 and frame coordinate system 70 can be determined during a calibration sequence of the inspection system.

FIG. 5 illustrates by set of 3×3 images 30(n−1, m1)-30(n+1, m+1) that cover die 14(0,0) as well as its proximate vicinity. FIG. 5 illustrates that images 30(n1, m−1) includes unique feature 34(0,0,1), image 30(n+1, m−1) includes unique feature 34(0,0,2), image 30(n−1, m+1) includes unique feature 34(0,0,3) and image 30(n+1, m+1) includes unique feature 34(0,0,4). Image (n−1, m) includes a part of unique feature 34(3,3,1) and image 30(n+1, m) includes a part of unique feature 34(0,0,4).

Figure 6:
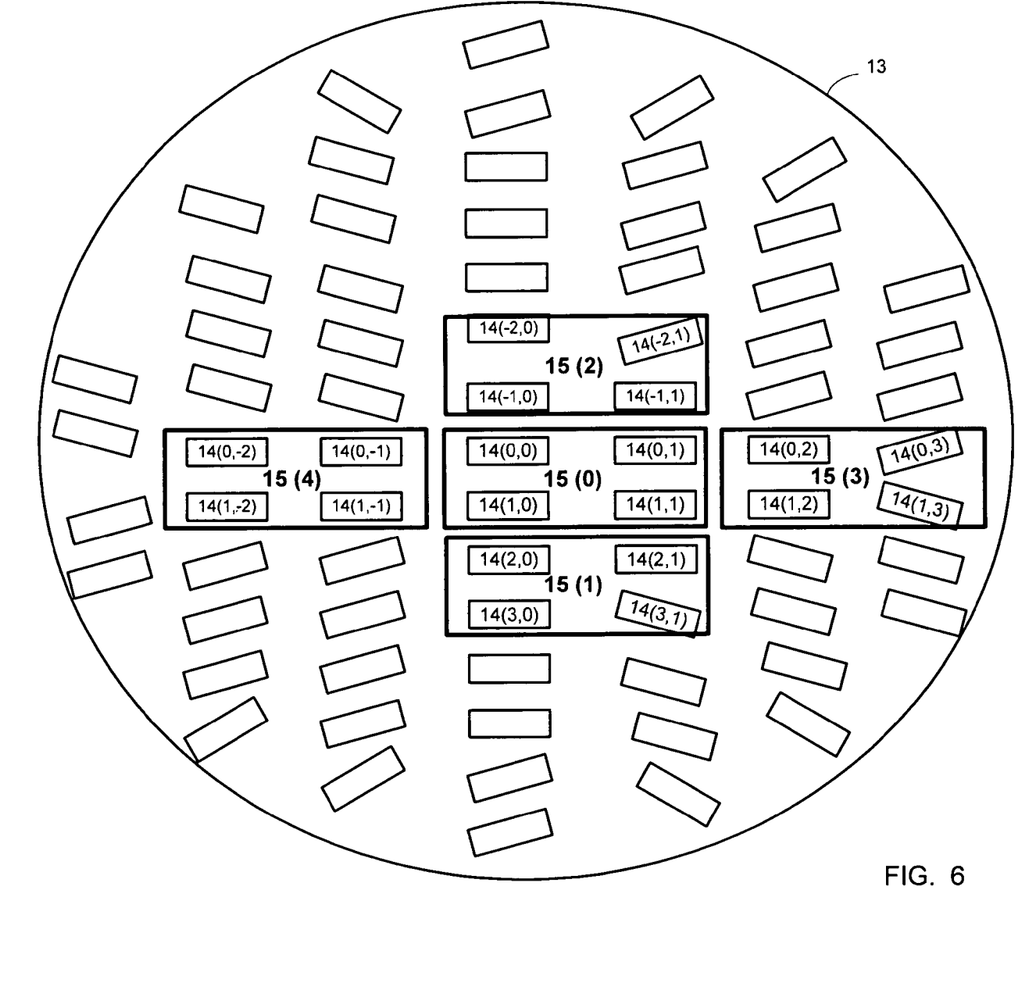
FIG. 6 illustrates the dice indices assignment in a diced wafer as part of a die alignment process according to an embodiment of the invention.

FIG. 6 illustrates the dice indices assignment in a diced wafer 13 as part of a die alignment process. The die alignment process defines for each die a unique index and the die location.

For setting the die alignment process order, all scanned frames are organized by successive portions of the diced object—also referred to as processing groups. Processing groups are collectively denoted 15. Processing groups 15 are arranged so that each processing group is adjacent to one or more previous processing groups. Other considerations, such as mechanical constrains, may affect this arrangement. The arrangement of the frames to processing groups may be affected or not by predefined image acquisition scheme.

Each processing group 15 conveniently includes one or more dice and especially can include few dice, in order to prevent errors in the assignment of die indices and reference dice indices. A processing group can include dice that are located in a stripe shaped area but this is not necessarily so.

The first processing group includes frames near a specific location called an Alignment Area 15(0), which is an area that includes at least one die with position known in Global Coordinate System 20, as well as known index in the Reference Wafer Map.

Conveniently, Alignment Area 15(0) is defined at the middle of the diced wafer where the stretching forces are minimal, thus the movements of the center dies is minimal. Accordingly, the scanning pattern can start from the alignment area (preferably middle wafer) outwards. A user or operator of a system can provide the alignment area coordinates. The alignment area can differ from the center of the frame.

This scanning pattern is based upon the assumption that die pitch varies throughout the wafer. Dice in small area only may be approximated as rigid grid. Typically, neither orthogonal nor affine transformation may represent the whole wafer and therefore indexing of dice and local alignment is required.

Image acquisition can include scanning adjacent portions of the diced object, one after the other and assigning indexes, starting from dice in the alignment area and then one adjacent die after the other. In other words—the indexes are assigned to a continuous sequence of dies.

The image acquisition process can scan one adjacent portion of the diced object after the other and assign indexes to dies within one processing group after the other. The image acquisition and index assignment can be executed in a parallel manner. Conveniently, a portion can be imaged before all dies of a previously images portion were assigned indexes. For example—a first portion that includes processing group 15(3) can be images before all dies of processing groups 15(2) and 15(1) are assigned indexes.

The die alignment process for the alignment area will start immediately after or during image acquisition. For every processing group other than the $1^{st}$ one, the die alignment process will start after the die alignment process of the previous processing group has been completed. Location estimation for the dice in each frame will be based on previously collected information.

FIG. 6 illustrates 5 processing groups, each contains 4 dice. The dice indices in the first processing group, which is the alignment area, are: 14(0,0),14(0,1),14(1,0) and 14(1,1). The next processing group in FIG. 6 is 15(1) which is below and adjacent to 15(0), but it can be any other of the adjacent processing groups: either 15(2)—above, 15(3)—on the right or 15(4)—on the left.

Conveniently, dice indices are assigned in a gradual manner, to one processing group after the other, starting from alignment area 15(0) and then to dice located within other processing groups, wherein the dice indices assignment starts from one or more processing groups that are proximate to the alignment area and ending at processing groups that are located near the edge of the diced wafer.

FIG. 6 illustrate dice indices 14(−2,0) up to 14(3,1) that have been assigned to processing groups that are proximate to the alignment area and the alignment area itself.

The dice location information may be used for other equipment activities (die marking, another scan etc.) or may be exported for external use by other equipment or processes (the data may be used for process control purposes as well).

Figure 7A:
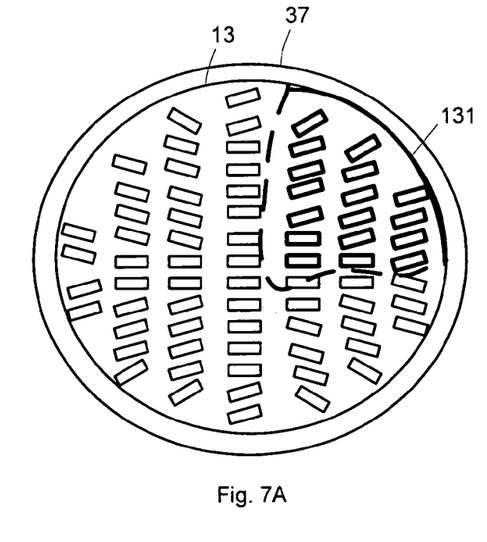
FIGS. 7A, 7B, 7C illustrate a partial wafer according to an embodiment of the invention.
Figure 7B:
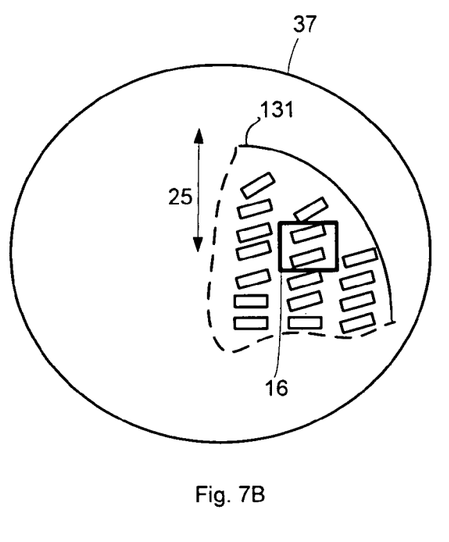
Figure 7C:
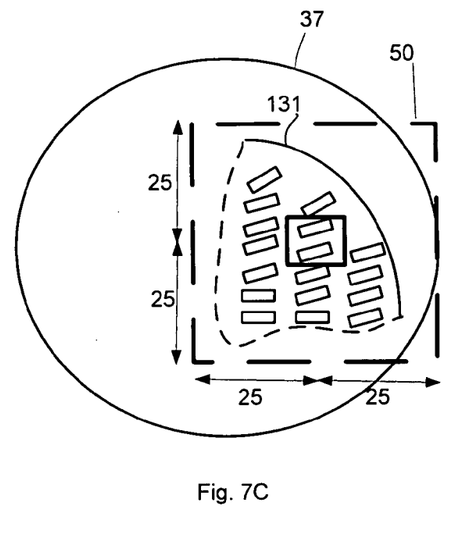

FIGS. 7A, 7B, 7C illustrate a partial wafer 131, which is a fraction of a wafer or can also represent a region of interest in a whole diced wafer that requires re-evaluation.

Partial wafer 131 is indicated in FIG. 7A as a darker area in the whole wafer.

FIG. 7B illustrates partial wafer 131 that can be placed in any position at tape 37 for further die alignment processing and/or inspection. There are two predefined parameters for the partial wafer scanning: alignment area 16 and a radius 25 measured from the alignment area.

The partial wafer 131 is much smaller than frame 37. In order to locate it the entire frame 37 can be scanned or only a portion thereof. A search area can be defined to include either the entire frame 37 of a significant portion thereof—in which at least a portion of the partial wafer can be found—as the partial wafer 137 can be located in an arbitrary manner on frame 37.

The search area can be defined based upon the location of the alignment area and an expected size of the partial wafer. For example—if the alignment area is located at the center of frame 37 and the partial wafer is about one fourth of the wafer then a search area that is coaxial with the center of frame 37 and has a radius of about one half of the radius of frame 37 can be defined.

The search area can be determined by scanning the search area 37 by a low resolution camera in order to obtain a rough estimation of the image area to be imaged by a high resolution camera in order to perform the defect detection. It is noted that both cameras can be replaced by a single camera that can operate at different resolutions—starting from low resolution and ending at a high resolution.

It is noted that the scanning can be replaced by acquiring images of entire areas of the frame.

FIG. 7C illustrates search area 50 that "covers" at least the partial wafer area with a threshold.

Search area 50 can also be defined by using a low resolution camera that performs a fast pre-scan to determine the size of the partial wafer area.

Figure 7D:
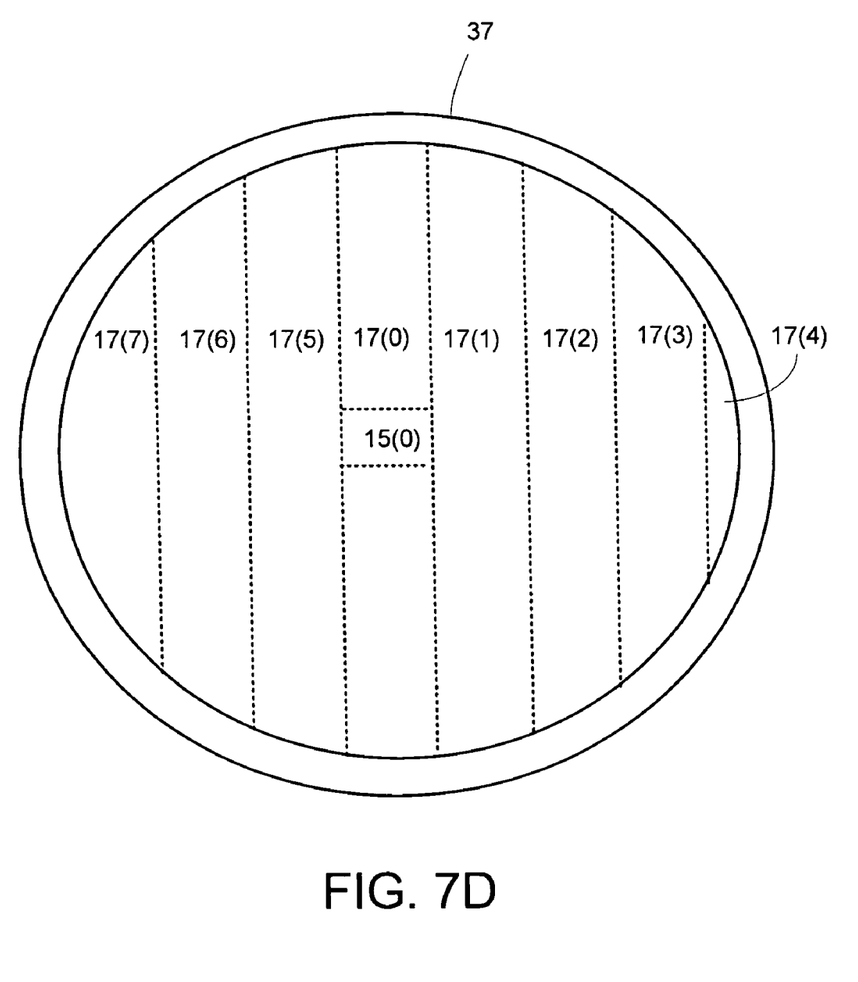
FIG. 7D-7G illustrate examples for image acquisition pattern according to different embodiment of the invention.

FIG. 7D illustrates multiple vertical strips 17(0)-17(7) that define an image acquisition pattern. These strips can be overlapping. Each strip can include one or more processing groups.

The image acquisition pattern starts by stripe 17(0) that includes alignment area 15(0). This is followed by scanning adjacent stripes 17(1), 17(2), 17(3) and 17(4). The scanning pattern then scans stripes 17(5), 17(6) and 17(7). Thus—one stripe after the other are scanned in order to provide a consecutive sequence of images portions of the diced wafer—starting from scanning portions at one side of alignment area 15(0) and then scanning portions at the other side of alignment area 15(0).

The image acquisition pattern can also be an alternating one. For Example—stripes can be scanned according to the following order: 17(0), 17(1), 17(5), 17(2), 17(6), 17(3), 17(7) and 17(4). It is noted that the scanning can also alternate each few stripes. For example—17(0), 17(1), 17(2), 17(5), 17(6), 17(3), 17(4) and 17(7).

Figure 7E:
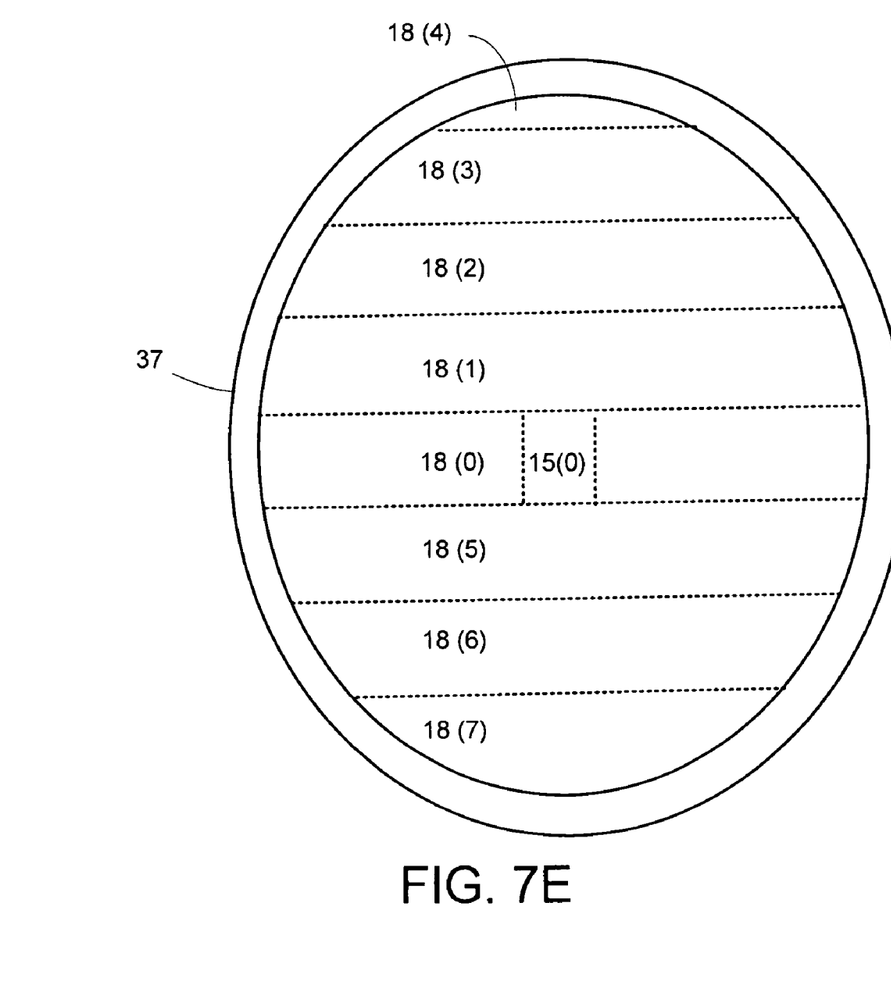

FIG. 7E illustrates multiple horizontal strips 18(0)-18(7) that define an image acquisition pattern.

These strips can be overlapping. Each strip can include one or more processing groups.

The image acquisition pattern starts by stripe 18(0) that includes alignment area 15(0). This is followed by scanning adjacent stripes 18(1), 18(2), 18(3) and 18(4). The scanning pattern then scans stripes 18(5), 18(6) and 18(7). Thus—one stripe after the other are scanned in order to provide a consecutive sequence of images portions of the diced wafer—starting from scanning portions at one side of alignment area 15(0) and then scanning portions at the other side of alignment area 15(0).

The image acquisition pattern can also be an alternating one. For Example—stripes can be scanned according to the following order: 18(0), 18(1), 18(5), 18(2), 18(6), 18(3), 18(7) and 18(4). It is noted that the scanning can also alternate each few stripes. For example—18(0), 18(1), 18(2), 18(5), 18(6), 18(3), 18(4) and 18(7).

Figure 7F:
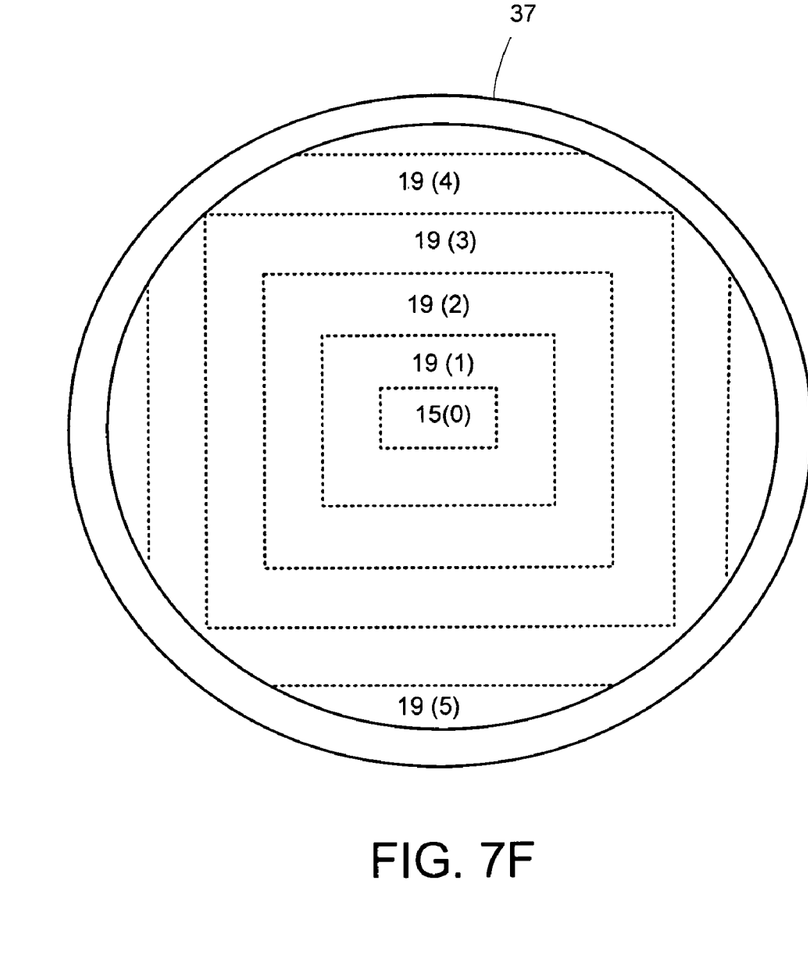

FIG. 7F illustrates alignment area 15(0) and multiple coaxial rectangular portions 19(1)-19(5) that define an image acquisition pattern.

These portions can be overlapping. Each portion can include one or more processing groups.

The image acquisition pattern starts by alignment area 15(0). This is followed by scanning adjacent stripes 19(1), 19(2), 19(3), 19(4) and 19(5)—one after the other. Each portion requires two opposing vertical scans and two opposing horizontal scans. For example, assuming that portion 19(1) is being scanned from its upper right corner than the scanning starts by a right to left scan that is followed by a top to bottom scan, then a left to right scan and finally a bottom to top scan.

Figure 7G:
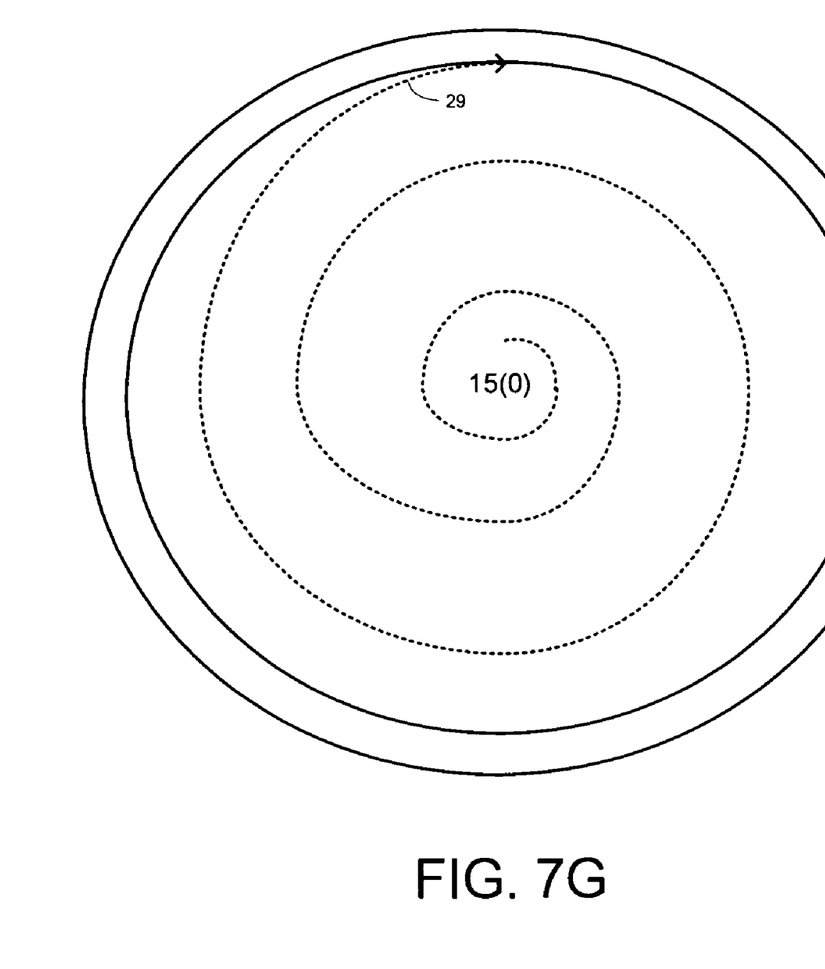

FIG. 7G illustrates alignment area 15(0) and a spiral scan pattern that is illustrated by dashed line 29.

It is noted that the die alignment process described in FIG. 6 can be applied to partial wafer 131 as well as a whole diced wafer. Partial wafer can be compared to a reference partial wafer or to a reference wafer that includes at least one partial wafer. A partial wafer can be provided if some dice of a wafer are not examined, cut off during the dicing process and the like. A partial wafer can also represent a region of interest in a diced wafer that should be evaluated or even re-evaluated.

A partial wafer shall include at least 2 unique features. The processing of images of the partial wafer can include looking for unique features, using the unique features for wafer alignment, starting the scanning pattern from (or near to) the alignment area.

Images of a partial wafer can be scanned after the whole wafer is scanned. In this case information from the previous scan (of the whole wafer) can be used.

Figure 8:
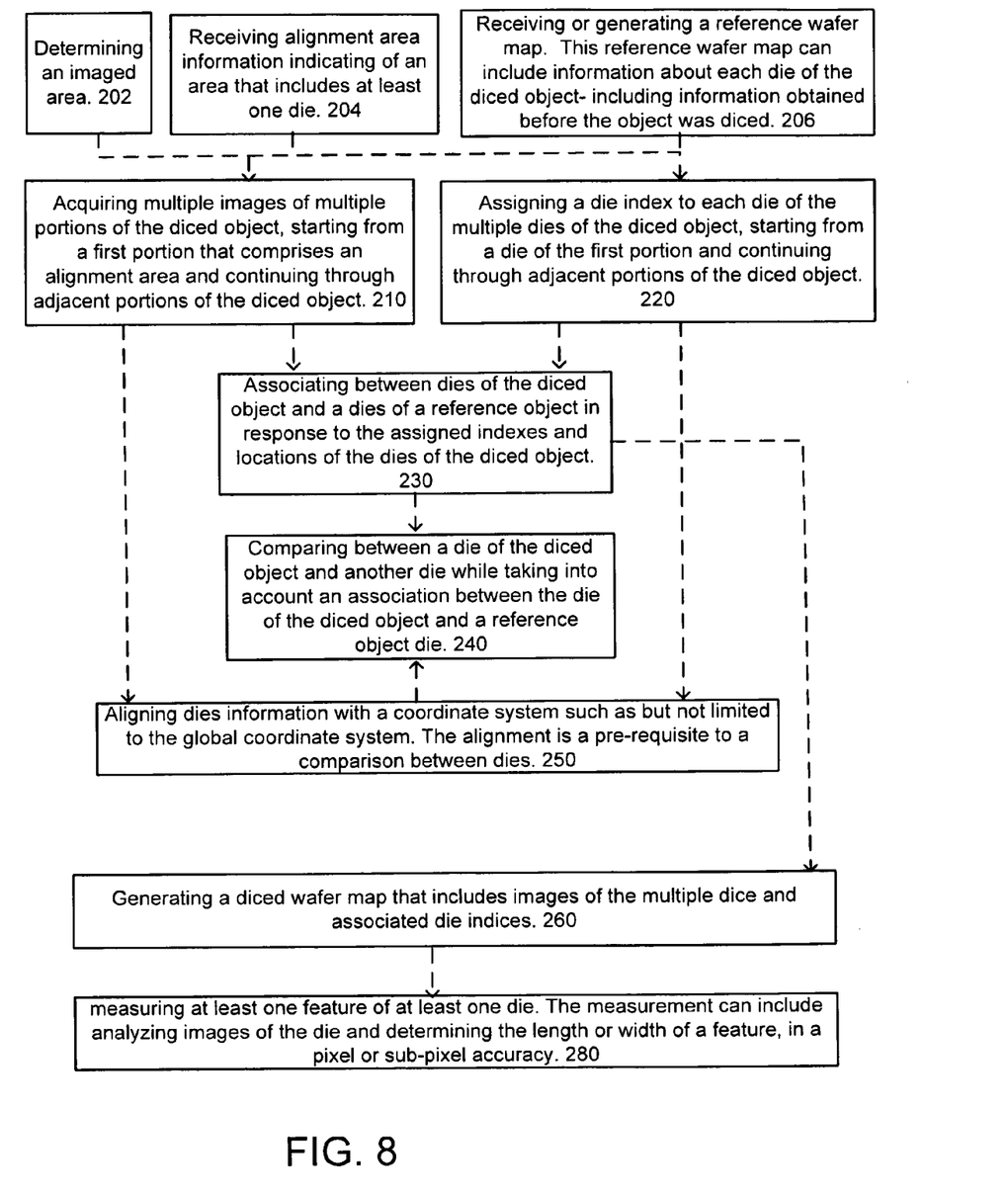
FIG. 8 illustrates a method for inspecting a wafer according to an embodiment of the invention.

FIG. 8 illustrates method 200 for inspecting a diced wafer, according to an embodiment of the invention.

Method 200 can start by any stage of stages 202, 204, 206, 210 and 220. For simplicity of explanation stage 210 and 220 are illustrated as following stages 202, 204 and 206.

Stage 202 includes determining an imaged area. Stage 202 can include determining the images area by scanning a search area that is larger than the image area by a low resolution camera.

Stage 204 includes receiving alignment area information indicating of an area that includes at least one die. Stage 204 can be followed by stage 210 and, additionally or alternatively, by stage 202. The alignment area can be positioned at a middle of search area that is defined by a frame that holds the diced object. Stage 204 can includes receiving alignment are information indicative of the location of the alignment area at the center of the frame.

Stage 206 includes receiving or generating a reference wafer map. This reference wafer map can include information about each die of the diced object—including information obtained before the object was diced.

The map can include index per each dies that are arranged in an ordered manner (if the map represents the object before being diced).

Stage 210 includes acquiring multiple images of multiple portions of the diced object, starting from a first portion that comprises an alignment area and continuing through adjacent portions of the diced object.

Stage 210 can include acquiring multiple images of multiple portions of the diced object, by scanning one stripe after the other.

Stage 210 can include: (i) obtaining an image of the first portion; (ii) obtaining images of adjacent portions located at one side of the first portion; and finally (iii) obtaining images of adjacent portions located at another side of the first portion. Referring to the example set fourth in FIG. 7D this can include acquiring images of stripe 17(0), 17(1), Stage 210 can include acquiring multiple images of multiple portions of the diced object, by: (i) obtaining an image of the first portion; (ii) obtaining, in an alternating manner, images of adjacent portions located at different sides of the first portion.

Stage 210 can include obtaining an image of the first portion and then obtaining images of adjacent portions in a spiral manner.

Stage 210 can include acquiring partially overlapping images.

Conveniently, stage 210 includes introducing a continuous mechanical translation between the diced wafer and an image acquisition unit. It is noted that the diced wafer can be illuminated by a continuous light source, by a pulsed light source, and an area illumination, by a spot light source, by applying bright field detection or dark field detection and the like.

Stage 220 includes assigning a die index to each die of the multiple dies of the diced object, starting from a die of the first portion and continuing through adjacent portions of the diced object.

Stage 220 can include assigning indexes to dies of a certain portion of the diced object before assigning indexes to the entire dies of a previously images portion of the diced object.

Stage 210 and 220 are followed by stage 230 of associating between dies of the diced object and a dies of a reference object in response to the assigned indexes and locations of the dies of the diced object. The reference object is not diced. Thus, each die can get an index that corresponds to the die index before the diced object was diced.

Stage 230 is followed by stage 240 of comparing between a die of the diced object and another die while taking into account an association between the die of the diced object and a reference object die.

The other die can belong to the diced object, to another diced object or a non-diced object. It can be a golden die.

Stage 240 can provide a comparison result that is indicative of defects.

The can diced object is a partial wafer and stage 210 can include acquiring images within an imaged area.

Stage 220 can include assigning a die index to each die and estimating die location of the die using previously collected information.

Stages 210 and 220 can also be followed by stage 250 of aligning dies information with a coordinate system such as but not limited to the global coordinate system. The alignment is a pre-requisite to a comparison between dies.

Stage 250 can be executed in parallel to stage 230 but this is not necessarily so.

Stage 250 can include locating multiple unique features within the multiple images.

Conveniently, stage 250 includes applying normalized correlation or geometric hashing. Geometric hashing is described in the following articles and patents, all being incorporated herein by reference: "Rehashing for Bayesian Geometric Hashing", M. Lifshits, I. Blayvas, R. Goldenberg and E. Rivlin, Proceedings of the 17th international conference on pattern recognition (ICPR'04), "Geometric Hashing: An Overview, H. J. Wolfson and I. Rigoutsos, IEEE Computational Science & Engineering, 1997 IEEE, U.S. Pat. No. 6,941,016 of Wagman et al., U.S. Pat. No. 7,027,651 of Simon et al., and U.S. Pat. No. 6,993,192 of Silver Conveniently, stage 250 includes applying multiple image recognition techniques. Conveniently, stages 220 and 250 partially overlap. Accordingly, while certain images are acquired, unique features within previously acquired images can be located.

Stage 210 can include determining positions of multiple dice in response to locations of the multiple unique features and in response to and at least one die uncertainty parameter. The at least one die uncertainty parameter can reflect the rotations, shifts and movements of a die during the sawing and expanding process.

Stage 230 can be followed by stage 260 of generating a diced wafer map that includes images of the multiple dice and associated die indices. Stage 260 can include updating a reference wafer map by the images of the die of the diced object.

Stage 260 can include generating a diced wafer map that includes positions of the multiple dice in the global coordinate system.

Conveniently, stage 260 can include performing a registration of the diced wafer map in relation of a reference wafer map.

Conveniently, each die is characterized by a die coordinate system so stage 260 can include calculating a coordinate transformation from each die coordinate system to global coordinate system 20.

Conveniently, stage 260 includes determining a relationship between each die coordinate system to a frame coordinate system. The coordinate transformation is responsive to the determined relationship and to a relationship between the global coordinate system and the frame coordinate system. The relationship between the global coordinate system and the image acquisition system can be determined during an inspection system calibration session.

Conveniently, stage 250 of locating multiple unique features and stage 220 of assigning multiple die indexes include a sequence of index assignment stages and unique feature detection.

Conveniently, stage 240 can include detecting defects based upon a comparison between pixels of a die image and pixels of an associated reference die image.

Conveniently, stages 210 and 220 are followed by stage 280 of measuring at least one feature of at least one die. The measurement can include analyzing images of the die and determining the length or width of a feature, in a pixel or sub-pixel accuracy.

Figure 9:
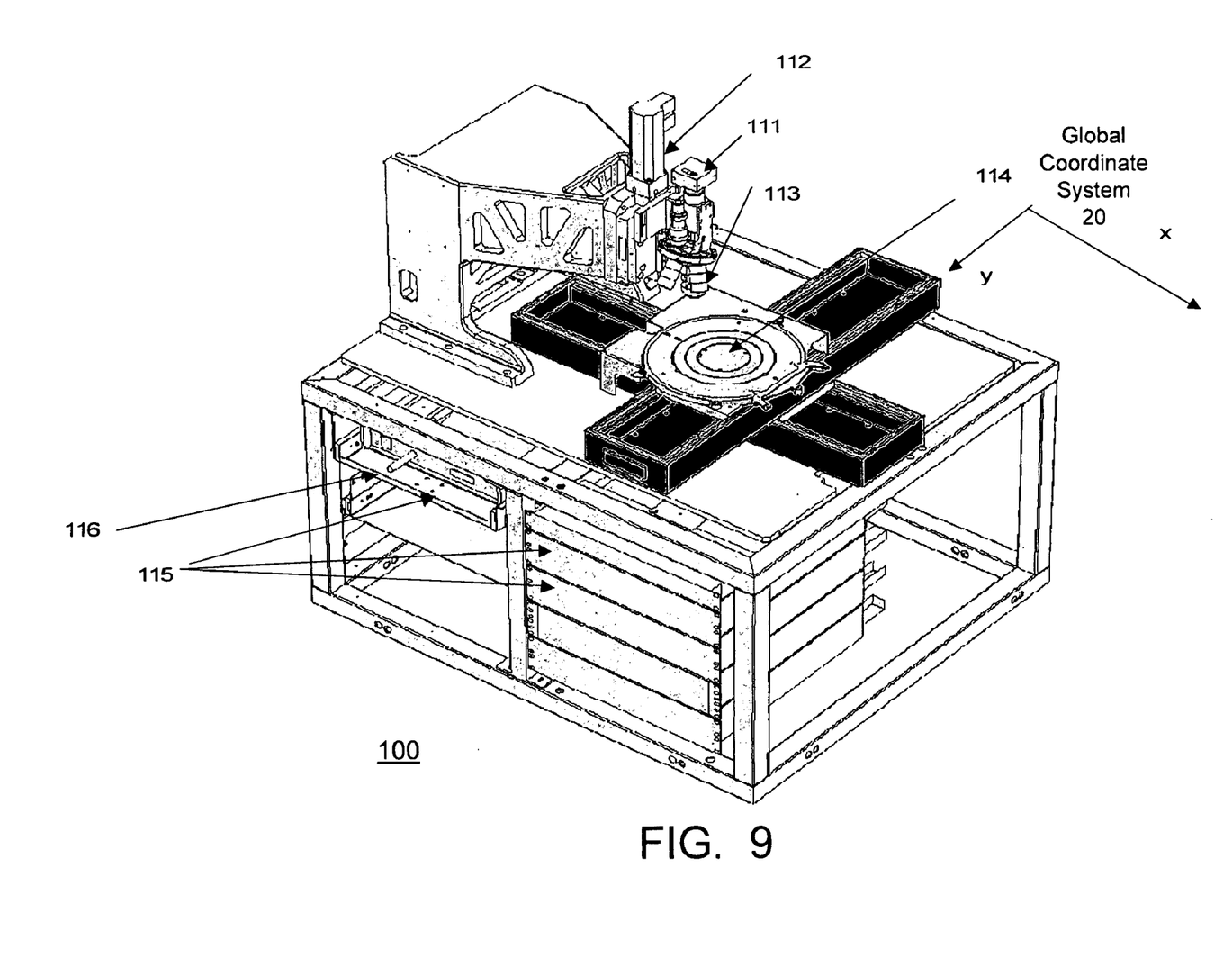
FIG. 9 illustrates a system, according to an embodiment of the invention.

FIG. 9 illustrate system 100 according to an embodiment of the invention. System 100 includes image acquisition unit 111, processor 115, illuminator 112, optics 113, a mechanical stage such as X-Y table 114 and storage unit 116.

System 100 can define or receive a predefined image acquisition scheme and accordingly scan the diced wafer while acquiring images.

For cases of inspecting a partial wafer, system 100 includes a low resolution camera (not shown). The definition of the image acquisition scheme includes using the low resolution camera for a fast pre-scan, so as to determine the borders of the image acquisition scheme.

X-Y table 114 is adapted to introduce a continuous mechanical translation between the diced wafer and the image acquisition unit.

Image acquisition unit 111 can include one or more detectors that can acquire an image of an area illuminated by illuminator 112. Optics 13 may serve the illumination of a diced wafer (placed on X-Y table 114) as well as serve for collecting light and directing it towards image acquisition unit 111. Storage unit 116 stored acquired images and is accessible by processor 115. It is noted that the detection signals from image acquisition unit 111 can be processed by processor 115 in order to provide images (or frames)

The diced wafer can be illuminated by overlapping strobes of light that forming overlapping images of frames.

The motion of X-Y table 114 is managed electronically by high precision control system, this enables to correlate the exact location of each pixel in the scanned object (image) in relation to global coordinate system 20.

Conveniently, image acquisition unit 112 is adapted to acquire multiple images of multiple portions of a diced wafer that include multiple dice while processor 115 is adapted to: (i) locate multiple unique features within the multiple images, (ii) assign a die index to each dice of the multiple dice; and (iii) associate between the multiple dice and multiple reference dice in response to locations of the multiple unique features, to at least one expected die.

Conveniently processor 115 is adapted to: assign a die index to each die of the multiple dies of the diced object, starting from a die of the first portion and continuing through adjacent portions of the diced object; associate between dies of the diced object and a dies of a reference object in response to the assigned indexes and locations of the dies of the diced object; wherein the reference object is not diced; and compare between a die of the diced object and another die while taking into account an association between the die of the diced object and a reference object die.

Processor 115 can also perform at least one of the following operations, or a combination thereof: (i) estimate die location using previously collected information; (ii) determine positions of multiple dice in response to locations of the multiple unique features and in response to at least one die uncertainty parameter; (iii) generate a diced wafer map that includes images of the multiple dice and associated die indexes; (iv) calculate a coordinate transformation from each die coordinate system to a global coordinate system; (v) determine a relationship between each die coordinate system to a frame coordinate system; wherein the coordinate transformation is responsive to the determined relationship and to a relationship between the global coordinate system and the frame coordinate system; (vii) perform a registration of the diced wafer map in relation of a reference wafer map; (viii) detect defects based upon a comparison between pixels of a dice image and pixels of an associated reference dice image; (ix) locate at least one unique feature while the image acquisition unit acquires at least one image; (x) associate between at least one die and at least one reference die while the image acquisition unit acquires at least one image; (xi) locate at least one unique feature by applying normalized correlation or geometric hashing; (xii) locate at least one unique feature by applying multiple image recognition techniques; or (xiii) measure at least one feature of at least one die.

It is noted that memory unit 116 can also store images of the reference dice as well as information (such as 5 die index) relating to the acquired images of the dice of the diced wafer. It can store a reference wafer map, and alternatively or additionally the diced wafer map.

Image acquisition unit 111 can include one or more line sensors, point sensors, two dimension sensor arrays and the like. Illuminator 112 can include a laser source a lamp, can provide light pulses or continuous illumination, can illuminate a spot or illuminate an area. Illuminator 112 is illustrated as bright field illuminator but system 100 can apply, additionally or alternatively, dark filed illumination.

Processor 115 can also control the operation of the various components of system 100 but this is not necessarily so and system 100 can include one or other controllers that control the operation of system 100.

Conveniently, processor 115 can include multiple components that can operate in parallel in order to increase the processing speed of system 100. These components can perform the same function or different functions.

Conveniently, storage unit 116 may include one or multiple storage components that be accessed serially or in a parallel manner, for speeding to processing speed of system 100. Different storage unit components can store different type of information or the same type of information.

Although the invention has been described in conjunction with specific embodiments thereof, it is evident that many alternatives, modifications and variations will be apparent to those skilled in the art, accordingly, it is intended to embrace all such alternatives, modifications and variations that fall within the spirit and broad scope of the appended claims.

We claim:

1. A method for inspecting a diced object that comprises multiple dies, the method comprises:
   acquiring by an image acquisition unit multiple images of multiple portions of the diced object, starting from a first portion that comprises an alignment area and continuing through adjacent portions of the diced object; wherein the alignment area is used for aligning dies information with a coordinate system such as the global coordinate system; and wherein the acquiring of the multiple images comprises illuminating the diced wafer;
   assigning by a processor a die index to each die of the multiple dies of the diced object, starting from a die of the first portion and continuing through adjacent portions of the diced object; wherein the indexes are assigned to a continuous sequence of dies;
   associating by the processor between dies of the diced object and a die of a reference object in response to the assigned indexes and locations of the dies of the diced object; wherein the reference object is not diced; and
   comparing by a processor between a die of the diced object and another die while taking into account an association between the die of the diced object and a reference object die.

2. The method according to claim 1 wherein the diced object is a partial wafer and the acquiring comprises acquiring images within an imaged area.

3. The method according to claim 2 wherein the imaged area is determined by scanning by the image acquisition unit a search area that is larger than the image area by a low resolution camera.

4. The method according to claim 1 comprising receiving by a system that comprises the processor and the image acquisition unit alignment area information indicating of an area that includes at least one die.

5. The method according to claim 1 wherein the alignment area is positioned at a middle of search area that is defined by a frame that holds the diced object.

6. The method according to claim 1 comprising acquiring by the image acquisition unit multiple images of multiple portions of the diced object, by scanning one stripe after the other.

7. The method according to claim 1 comprising acquiring by the image acquisition unit multiple images of multiple portions of the diced object, by:
obtaining an image of the first portion;
obtaining images of adjacent portions located at one side of the first portion; and
obtaining images of adjacent portions located at another side of the first portion.

8. The method according to claim 1 comprising acquiring by the image acquisition unit multiple images of multiple portions of the diced object, by:
obtaining an image of the first portion;
obtaining, in an alternating manner, images of adjacent portions located at different sides of the first portion.

9. The method according to claim 1 comprising acquiring by the image acquisition unit multiple images of multiple portions of the diced object, by obtaining an image of the first portion and then obtaining images of adjacent portions in a spiral manner.

10. A system for inspecting a diced object that comprises multiple dies, the system comprises:
an image acquisition unit configured to acquire multiple images of multiple portions of the diced object, wherein acquiring comprises aligning dies information with a coordinate system such as the global coordinate system; starting from a first portion that comprises an alignment area and continuing through adjacent portions of the diced object;
a processor, configured to:
assign a die index to each die of the multiple dies of the diced object, starting from a die of the first portion and continuing through adjacent portions of the diced object; wherein the indexes are assigned to a continuous sequence of dies;
associate between dies of the diced object and a die of a reference object in response to the assigned indexes and locations of the dies of the diced object; wherein the reference object is not diced; and
compare between a die of the diced object and another die while taking into account an association between the die of the diced object and a reference object die.

11. The system according to claim 10 wherein the diced object is a partial wafer and the system is configured to acquire images within an imaged area.

12. The system according to claim 11 comprising a low resolution camera;
wherein the system determines the imaged area by scanning a search area that is larger than the image area by the low resolution camera.

13. The system according to claim 10 configured to receive alignment area information indicating of an area that includes at least one die and in response image the alignment area.

14. The system according to claim 10 configured to start acquiring images from an alignment area that is positioned at a middle of search area that is defined by a frame that holds the diced object.

15. The system according to claim 10 configured to acquire multiple images of multiple portions of the diced object, by scanning one stripe after the other.

16. The system according to claim 10 configured to acquire multiple images of multiple portions of the diced object, by:
obtaining an image of the first portion;
obtaining images of adjacent portions located at one side of the first portion; and
obtaining images of adjacent portions located at another side of the first portion.

17. The system according to claim 10 configured to acquire multiple images of multiple portions of the diced object, by:
obtaining an image of the first portion;
obtaining, in an alternating manner, images of adjacent portions located at different sides of the first portion.

18. The system according to claim 10 configured to acquire multiple images of multiple portions of the diced object, by acquiring multiple images of multiple portions of the diced object, by obtaining an image of the first portion and then obtaining images of adjacent portions in a spiral manner.

19. The method according to claim 1 comprising introducing a continuous mechanical translation between the diced wafer and the image acquisition unit during the acquiring by the image acquisition unit multiple images of multiple portions of the diced object.

* * * * *